United States Patent
Wilson et al.

(10) Patent No.: US 11,246,623 B2
(45) Date of Patent: *Feb. 15, 2022

(54) VISUALIZATION DEVICES FOR USE DURING PERCUTANEOUS TISSUE DISSECTION AND ASSOCIATED SYSTEMS AND METHODS

(71) Applicant: InterVene, Inc., South San Francisco, CA (US)

(72) Inventors: Fletcher T. Wilson, San Francisco, CA (US); David Batten, Los Gatos, CA (US); Zachary J. Malchano, San Francisco, CA (US)

(73) Assignee: InterVene, Inc., South San Francisco, CA (US)

( * ) Notice: Subject to any disclaimer, the term of this patent is extended or adjusted under 35 U.S.C. 154(b) by 367 days.

This patent is subject to a terminal disclaimer.

(21) Appl. No.: 16/222,718

(22) Filed: Dec. 17, 2018

(65) Prior Publication Data

US 2019/0321064 A1    Oct. 24, 2019

Related U.S. Application Data

(62) Division of application No. 14/667,201, filed on Mar. 24, 2015, now Pat. No. 10,188,419.
(Continued)

(51) Int. Cl.
*A61B 17/3203* (2006.01)
*A61B 17/00* (2006.01)
(Continued)

(52) U.S. Cl.
CPC ............ *A61B 17/3203* (2013.01); *A61B 8/12* (2013.01); *A61B 8/4494* (2013.01);
(Continued)

(58) Field of Classification Search
CPC .... A61B 17/3203; A61B 2017/320044; A61B 2017/00106–0011; A61B 8/12; A61B 8/445; A61B 8/4494
See application file for complete search history.

(56) References Cited

U.S. PATENT DOCUMENTS 3,704,711 A    12/1972 Park
4,898,574 A    2/1990 Uchiyama et al.
(Continued)

FOREIGN PATENT DOCUMENTS

CA    1281381 C    3/1991
CA    2678971 A1   8/2008
(Continued)

OTHER PUBLICATIONS

Corcos, I., "A new autologous venous valve by intimal flap: One cases report." Note Di Tecnica, Minerva Cardioangiol, 2003, 51, 10 pages.
(Continued)

*Primary Examiner* — James M Kish
(74) *Attorney, Agent, or Firm* — Perkins Coie LLP

(57) ABSTRACT

A device and method for visualization of the intravascular creation of autologous valves, and particularly venous valve, is disclosed herein. One aspect of the present technology, for example, is directed toward a delivery catheter that can include a lumen configured to receive a dissection assembly and a trough having a plurality of transducers electrically coupled to a proximal portion of the delivery catheter. At least one of the transducers can be configured to emit a signal towards a portion of a blood vessel adjacent the trough, and at least one of the transducers can be configured to receive a reflection of the emitted signal.

10 Claims, 10 Drawing Sheets

Related U.S. Application Data

(60) Provisional application No. 61/969,262, filed on Mar. 24, 2014, provisional application No. 61/969,263, filed on Mar. 24, 2014.

(51) Int. Cl.
*A61B 8/12* (2006.01)
*A61B 17/12* (2006.01)
*A61B 8/00* (2006.01)
*A61B 34/20* (2016.01)
*A61B 17/22* (2006.01)
*A61B 5/00* (2006.01)
*A61B 90/00* (2016.01)
*A61B 17/32* (2006.01)

(52) U.S. Cl.
CPC .. *A61B 17/00234* (2013.01); *A61B 17/12136* (2013.01); *A61B 17/22* (2013.01); *A61B 17/32037* (2013.01); *A61B 34/20* (2016.02); *A61B 5/0066* (2013.01); *A61B 5/0084* (2013.01); *A61B 17/12109* (2013.01); *A61B 2017/00292* (2013.01); *A61B 2017/00778* (2013.01); *A61B 2017/00783* (2013.01); *A61B 2017/22095* (2013.01); *A61B 2017/320044* (2013.01); *A61B 2090/3735* (2016.02); *A61B 2090/3784* (2016.02); *A61B 2562/043* (2013.01)

(56) References Cited

U.S. PATENT DOCUMENTS

| | | | |
|---|---|---|---|
| 4,932,962 | A | 6/1990 | Yoon et al. |
| 5,112,339 | A | 5/1992 | Zelman et al. |
| 5,190,046 | A | 3/1993 | Shturman et al. |
| 5,372,601 | A | 12/1994 | Banning et al. |
| 5,443,443 | A | 8/1995 | Shiber et al. |
| 5,464,395 | A | 11/1995 | Faxon et al. |
| 5,601,588 | A | 2/1997 | Tonomura et al. |
| 5,606,975 | A | 3/1997 | Liang et al. |
| 5,695,507 | A | 12/1997 | Auth |
| 5,738,901 | A | 4/1998 | Wang et al. |
| 5,795,322 | A | 8/1998 | Boudewijn |
| 5,810,847 | A | 9/1998 | Laufer et al. |
| 5,836,945 | A | 11/1998 | Perkins |
| 5,989,276 | A | 11/1999 | Houser et al. |
| 6,190,353 | B1 | 2/2001 | Makower et al. |
| 6,375,635 | B1 | 4/2002 | Moutafis et al. |
| 6,379,319 | B1 | 4/2002 | Garibotto et al. |
| 6,344,027 | B1 | 5/2002 | Goll |
| 6,475,226 | B1 | 11/2002 | Farrell et al. |
| 6,506,178 | B1 | 1/2003 | Schubart et al. |
| 6,514,217 | B1 | 2/2003 | Selmon et al. |
| 6,524,251 | B2* | 2/2003 | Rabiner ............ A61B 17/22012 600/439 |
| 6,676,665 | B2 | 1/2004 | Foley et al. |
| 6,685,648 | B2 | 2/2004 | Macaulay et al. |
| 6,692,466 | B1 | 2/2004 | Chow et al. |
| 6,702,744 | B2 | 3/2004 | Mandrusov et al. |
| 6,758,836 | B2 | 7/2004 | Zawacki et al. |
| 6,902,576 | B2 | 6/2005 | Drasler et al. |
| 7,008,411 | B1 | 3/2006 | Mandrusov et al. |
| 7,056,325 | B1 | 6/2006 | Makower et al. |
| 7,150,738 | B2 | 12/2006 | Ray et al. |
| 7,179,249 | B2 | 2/2007 | Steward et al. |
| 7,273,469 | B1 | 9/2007 | Chan et al. |
| 7,357,795 | B2 | 4/2008 | Kaji et al. |
| 7,517,352 | B2 | 4/2009 | Evans et al. |
| 7,775,968 | B2 | 8/2010 | Mathis |
| 7,780,592 | B2 | 8/2010 | Tronnes et al. |
| 7,918,870 | B2 | 4/2011 | Kugler et al. |
| 7,927,305 | B2 | 4/2011 | Yribarren et al. |
| 7,938,819 | B2 | 5/2011 | Atkinson et al. |
| 7,955,346 | B2 | 6/2011 | Mauch et al. |
| 8,025,655 | B2 | 9/2011 | Atkinson et al. |
| 8,083,727 | B2 | 12/2011 | Kugler et al. |
| 8,100,860 | B2 | 1/2012 | von Oepen et al. |
| 8,114,123 | B2 | 2/2012 | Brenzel et al. |
| 8,267,947 | B2 | 9/2012 | Ellingwood et al. |
| 8,323,261 | B2 | 12/2012 | Atkinson et al. |
| 8,460,316 | B2 | 6/2013 | Wilson et al. |
| 8,636,712 | B2 | 1/2014 | Atkinson et al. |
| 8,753,366 | B2* | 6/2014 | Makower ......... A61B 17/12109 606/185 |
| 9,320,504 | B2 | 4/2016 | Wilson et al. |
| 9,381,034 | B2 | 7/2016 | Kawwei |
| 9,545,289 | B2 | 1/2017 | Yu et al. |
| 10,874,413 | B2 | 12/2020 | Wilson et al. |
| 2001/0041899 | A1 | 11/2001 | Foster |
| 2002/0029052 | A1 | 3/2002 | Evans et al. |
| 2002/0072706 | A1 | 6/2002 | Hiblar et al. |
| 2002/0091362 | A1 | 7/2002 | Maginot et al. |
| 2002/0103459 | A1 | 8/2002 | Sparks et al. |
| 2004/0167558 | A1 | 8/2004 | Igo et al. |
| 2004/0215339 | A1 | 10/2004 | Drasler et al. |
| 2005/0014995 | A1 | 1/2005 | Amundson et al. |
| 2005/0075665 | A1 | 4/2005 | Brenzel et al. |
| 2005/0165466 | A1 | 7/2005 | Morris et al. |
| 2005/0273159 | A1 | 12/2005 | Opie et al. |
| 2006/0094929 | A1 | 5/2006 | Tronnes et al. |
| 2006/0136045 | A1 | 6/2006 | Flagle et al. |
| 2006/0156875 | A1 | 7/2006 | McRury et al. |
| 2006/0178646 | A1 | 8/2006 | Harris et al. |
| 2006/0184187 | A1 | 8/2006 | Surti |
| 2006/0235449 | A1 | 10/2006 | Schubart et al. |
| 2006/0271090 | A1 | 11/2006 | Shaked et al. |
| 2007/0005093 | A1 | 1/2007 | Cox et al. |
| 2007/0093780 | A1 | 4/2007 | Kugler et al. |
| 2007/0093781 | A1 | 4/2007 | Kugler et al. |
| 2007/0208368 | A1 | 9/2007 | Katoh et al. |
| 2008/0033467 | A1 | 2/2008 | Miyamoto et al. |
| 2008/0103480 | A1* | 5/2008 | Bosel ............... A61M 25/0021 604/513 |
| 2008/0228171 | A1 | 9/2008 | Kugler et al. |
| 2008/0228211 | A1 | 9/2008 | Gonon |
| 2008/0243065 | A1 | 10/2008 | Rottenberg et al. |
| 2009/0005793 | A1 | 1/2009 | Pantages et al. |
| 2009/0112059 | A1 | 4/2009 | Nobis et al. |
| 2009/0182192 | A1 | 7/2009 | Shiono et al. |
| 2009/0209910 | A1 | 8/2009 | Kugler et al. |
| 2009/0254051 | A1 | 10/2009 | von Oepen et al. |
| 2009/0270799 | A1 | 10/2009 | Seto et al. |
| 2010/0076476 | A1 | 3/2010 | To et al. |
| 2010/0152682 | A1 | 6/2010 | Mauch et al. |
| 2010/0152843 | A1 | 6/2010 | Mauch et al. |
| 2010/0256599 | A1 | 10/2010 | Kassab et al. |
| 2011/0264125 | A1* | 10/2011 | Wilson ................ A61B 90/02 606/159 |
| 2011/0264127 | A1 | 10/2011 | Mauch et al. |
| 2011/0264128 | A1 | 10/2011 | Mauch et al. |
| 2012/0143234 | A1 | 6/2012 | Wilson et al. |
| 2012/0289987 | A1 | 11/2012 | Wilson et al. |
| 2013/0066346 | A1 | 3/2013 | Pigott et al. |
| 2013/0103070 | A1 | 4/2013 | Kugler et al. |
| 2013/0116715 | A1 | 5/2013 | Weber |
| 2013/0216114 | A1 | 8/2013 | Courtney et al. |
| 2013/0317534 | A1 | 11/2013 | Zhou et al. |
| 2014/0012301 | A1 | 1/2014 | Wilson et al. |
| 2015/0057566 | A1* | 2/2015 | Vetter ................. A61B 10/06 600/566 |
| 2015/0094532 | A1 | 4/2015 | Wilson et al. |
| 2015/0265263 | A1 | 9/2015 | Wilson et al. |
| 2015/0342631 | A1 | 12/2015 | Wilson et al. |
| 2015/0359630 | A1 | 12/2015 | Wilson et al. |
| 2016/0166243 | A1 | 6/2016 | Wilson et al. |
| 2016/0235428 | A1 | 8/2016 | Wilson et al. |
| 2017/0035450 | A1 | 2/2017 | Wilson et al. |
| 2017/0035455 | A1 | 2/2017 | Wilson et al. |
| 2018/0000509 | A1 | 1/2018 | Wilson et al. |
| 2018/0214173 | A1 | 8/2018 | Wilson et al. |

(56) References Cited

U.S. PATENT DOCUMENTS

2018/0289441 A1 10/2018 Wilson et al.
2018/0333166 A1 11/2018 Wilson et al.

FOREIGN PATENT DOCUMENTS

| CN | 1907243 | A | 2/2007 |
|----|---------|---|--------|
| CN | 1957861 | A | 5/2007 |
| JP | 2002514111 | A | 5/2002 |
| JP | 2003033357 | A | 2/2003 |
| JP | 2003267160 | A | 9/2003 |
| JP | 2009165822 | A | 7/2009 |
| JP | 2009183516 | A | 8/2009 |
| RU | 2108751 | C1 | 4/1998 |
| RU | 2160057 | C2 | 12/2000 |
| WO | 99000059 | A1 | 1/1999 |
| WO | 2008/063621 | | 5/2008 |
| WO | 2010074853 | A1 | 7/2010 |
| WO | 2011106735 | A1 | 9/2011 |
| WO | 2012145444 | A2 | 10/2012 |
| WO | 2013119849 | A1 | 8/2013 |
| WO | 2014110460 | A1 | 7/2014 |

OTHER PUBLICATIONS

Lugli, et al., Neovalve construction in the deep venous incompetence. J. Vasc. Surg., Jan. 2009, 49(1), 156-62.
Maleti, O., Neovalve construction in postthrombotic syndrome. Journal of Vascular Surgery, vol. 34, No. 4, 6 pages.

\* cited by examiner

VISUALIZATION DEVICES FOR USE DURING PERCUTANEOUS TISSUE DISSECTION AND ASSOCIATED SYSTEMS AND METHODS

CROSS-REFERENCE TO RELATED APPLICATIONS

The present application is a continuation of U.S. patent application Ser. No. 14/667,201 filed Mar. 24, 2015, now U.S. Pat. No. 10,188,419, which claims the benefit of U.S. Provisional Application No. 61/969,262, filed Mar. 24, 2014 and U.S. Provisional Application No. 61/969,263, filed Mar. 24, 2014, the disclosures of which are incorporated herein by reference in their entireties.

TECHNICAL FIELD

The present technology relates generally to devices and methods for intravascular modification of body lumens. Many embodiments of the present technology relate to visualization devices, systems and methods for use during the intravascular creation of dissection pockets within blood vessels.

BACKGROUND

Controlled dissection of a body lumen wall is a necessary treatment component of many widespread medical conditions. For example, in order to bypass a chronic total occlusion (CTO) in the vascular system, the physician can use a catheter to enter and travel through a length of the blood vessel wall corresponding to the site of the occlusion. As another example, one course of treatment for venous reflux involves modification of the blood vessel wall to create a valve and/or valve leaflet and/or repair a faulty valve and/or valve leaflet. One method for autologous creation of a valve leaflet, for instance, includes accessing the treatment site (either surgically or intravascularly) and entering the vessel wall with a catheter to create a dissection pocket (e.g., a portion of a body lumen wall where the wall has been separated into two or more distinct layers) Depending on the procedure (e.g., bypassing a CTO, creating a leaflet, etc.), it can be advantageous to finely control the shape and size of the dissection pocket. Such control can be challenging, especially considering the thinness and fragility of most body lumen walls, the curvature of most body lumen walls, the presence of pathologic changes to body lumen walls, and the effects of local, dynamic blood flow. Accordingly, the devices, systems, and methods of the present technology address these challenges.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

DETAILED DESCRIPTION

Figure 1A:
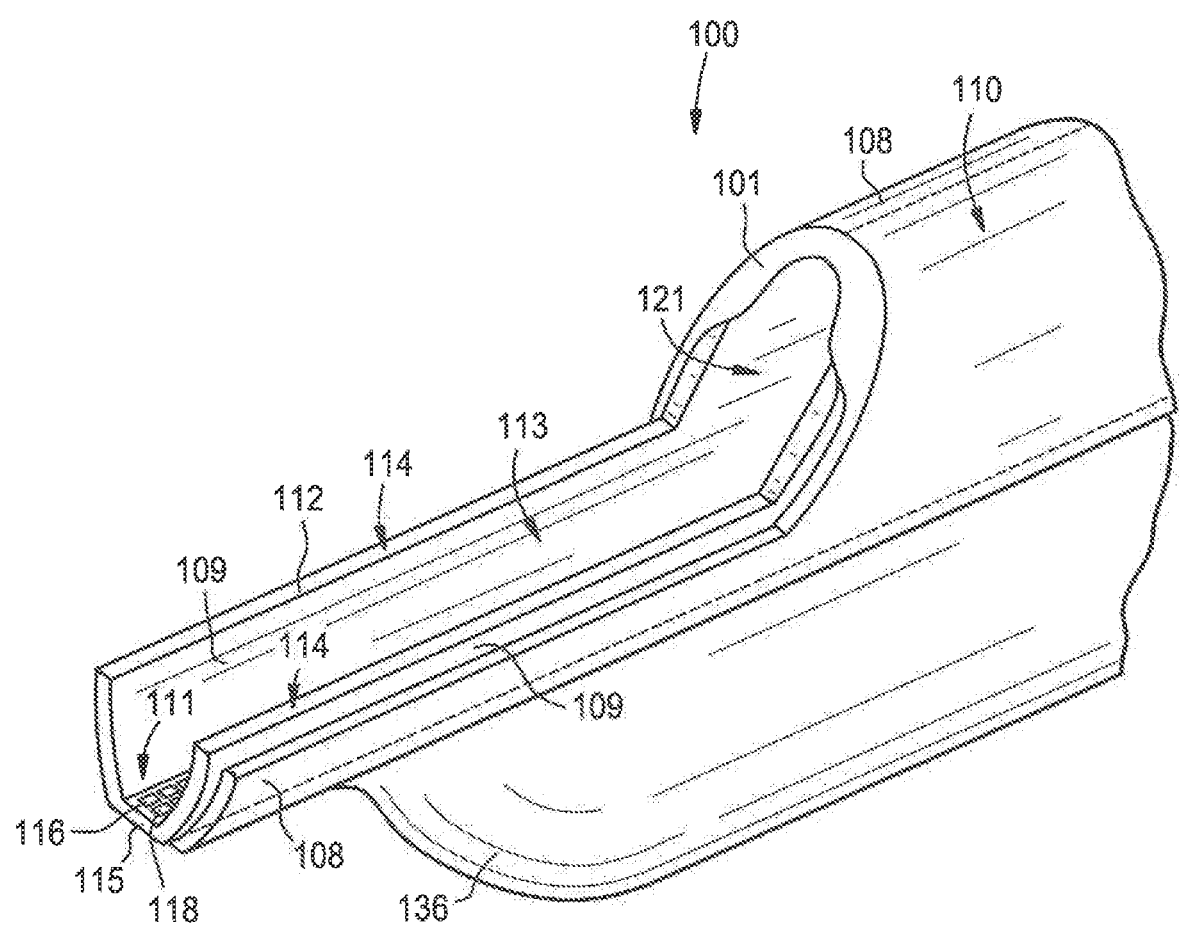
FIG. 1A is a perspective view of a delivery catheter in accordance with an embodiment of the present technology.

The present technology provides devices, systems, and methods for intravascular tissue dissection, such as creating dissection pockets within the wall of a body lumen. Specific details of several embodiments of treatment devices, systems and associated methods in accordance with the present technology are described below with reference to FIGS. 1A-6B. Although many of the embodiments are described below with respect to devices, systems, and methods for intravascular creation of autologous venous valves and/or valve leaflets, other applications and other embodiments in addition to those described herein are within the scope of the technology. For example, the present technology can be used in any body cavity or lumen or walls thereof (e.g., arterial blood vessels, venous blood vessels, urological lumens, gastrointestinal lumens, etc.), and for the surgical creation of autologous valves as well as the repair of autologous and/or synthetic valves. Additionally, several other embodiments of the technology can have different states, components, or procedures than those described herein. Moreover, it will be appreciated that specific elements, substructures, advantages, uses, and/or other features of the embodiments described with reference to FIGS. 1A-6B can be suitably interchanged, substituted or otherwise configured with one another in accordance with additional embodiments of the present technology. For example, the transducer array described with reference to FIGS. 1A-1C and/or the trough geometries shown in FIGS. 2A-2C can be combined with any of the delivery catheters and/or visualization devices shown in FIGS. 3A-3B. Likewise, the pocket creation element described in FIGS. 6A-6B can be combined with any of the delivery catheters described herein.

Furthermore, suitable elements of the embodiments described with reference to FIGS. 1A-6B can be used as standalone and/or self-contained devices. A person of ordinary skill in the art, therefore, will accordingly understand that the technology can have other embodiments with additional elements, or the technology can have other embodiments without several of the features shown and described below with reference to FIGS. 1A-6B. For example, the devices, systems, and methods of the present technology can be used with any of the catheter devices, systems, and methods disclosed in U.S. patent application Ser. No. 13/035,752, filed Feb. 2, 2011; U.S. patent application Ser. No. 13/035,818, filed Feb. 25, 2011; U.S. patent application Ser. No. 13/450,432, filed Apr. 18, 2012; U.S. Provisional Patent Application No. 61/969,262, filed Mar. 24, 2013; U.S. Provisional Patent Application No. 61/969,263, filed Mar. 24, 2013; U.S. patent application Ser. No. 13/926,886, filed Jun. 25, 2013; PCT Application No. PCT/US2014/011169, filed Jan. 10, 2014; U.S. patent application Ser. No. 14/377,492, filed Aug. 7, 2014; U.S. patent application Ser. No. 14/498,969, filed Sep. 26, 2014; and U.S. Provisional Patent Application No. 62/092,809, filed Dec. 16, 2014, all of which are incorporated by reference herein in their entireties (referred to collectively as "the Patents").

With regard to the terms "distal" and "proximal" within this description, unless otherwise specified, the terms can reference a relative position of the portions of a delivery catheter and/or an associated device with reference to an operator and/or a location in the vasculature.

Figure 1B:
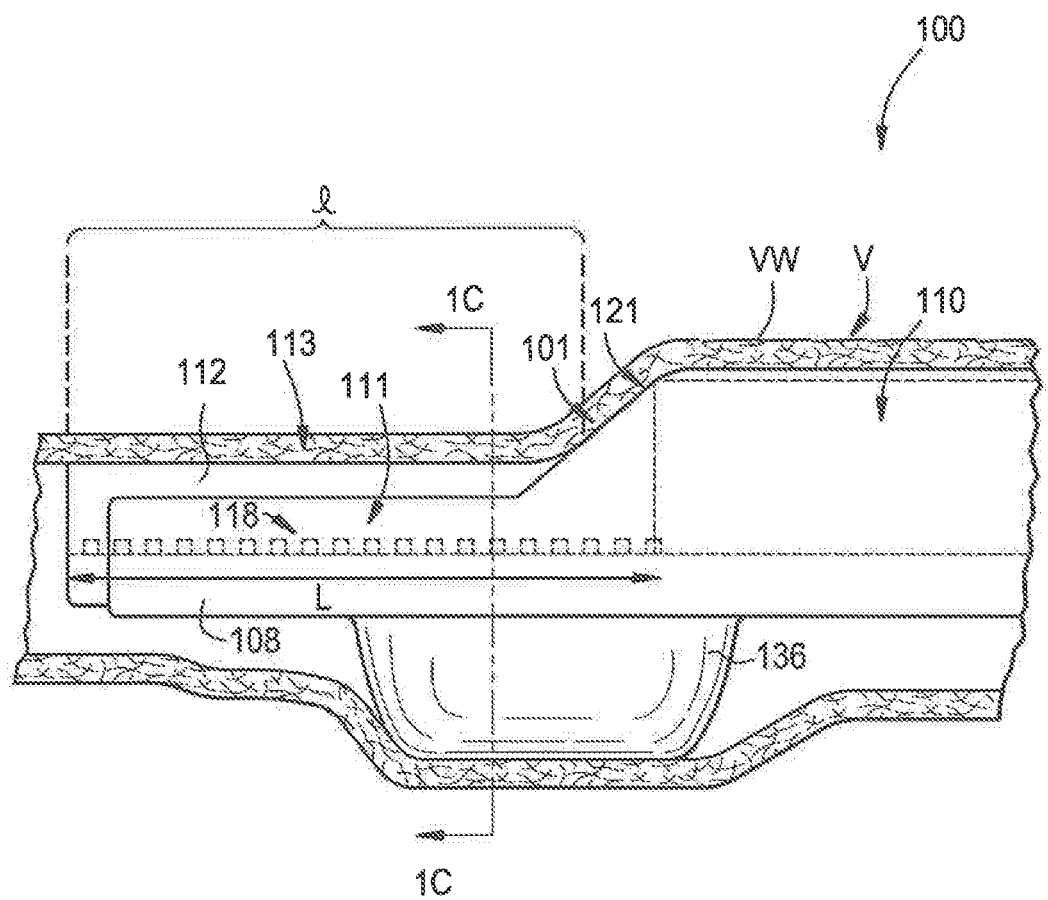
FIG. 1B is a side view of the delivery catheter of FIG. 1A in accordance with an embodiment of the present technology.
Figure 1C:
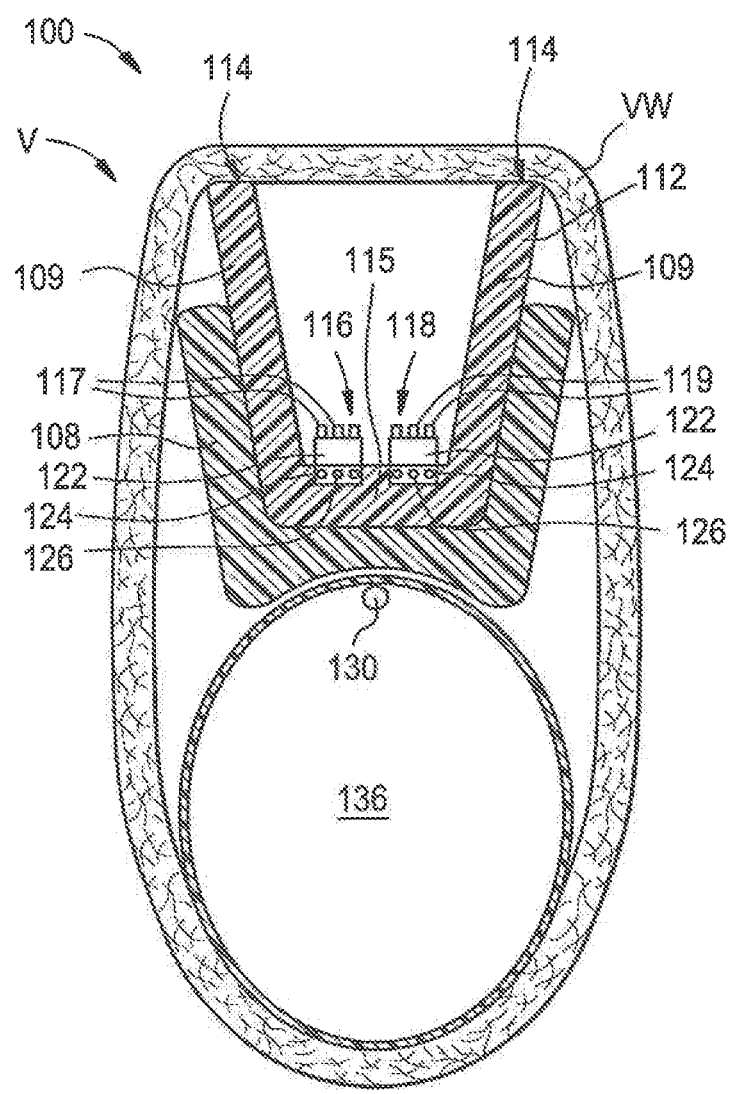
FIG. 1C is a cross-sectional end view of the delivery catheter of FIGS. 1A-1B taken along line 1C-1C in FIG. 1B.

FIG. 1A is a perspective view of a distal portion 100 of a delivery catheter in accordance with an embodiment of the present technology shown in an expanded state. A proximal portion (not shown) of the delivery catheter is configured to be positioned external to the patient while the distal portion 100 of the delivery catheter is positioned intravasculady at a treatment site. FIG. 1B is a side view of the distal portion 100 in the expanded state and positioned within a blood vessel V (e.g., a vein), and FIG. 1C is a cross-sectional end view of the distal portion 100 of FIG. 1B taken along line 1C-1C. Referring to FIGS. 1A-1C together, the delivery catheter can include a support 108, a device lumen 110 (not shown in FIG. 1C), an expansion lumen 130 (FIG. 1C), an expandable element 136 fluidly coupled to the expansion lumen 130, an open trough 112, and a transducer array 111 in the trough 112. In some embodiments, the expandable element 136 can be a balloon. In other embodiments, the expandable element 136 can be any expandable and/or inflatable structure (e.g., a wire cage, an expandable mesh, etc.).

The device lumen 110 is configured to slidably receive one or more interventional devices and extends distally from the proximal portion of the delivery catheter to an exit port 121 (FIG. 1A) positioned along a slanted surface 101 of the distal portion 100. For example, the device lumen 110 is configured to slidably receive a dissection assembly (not shown) configured to dissect at least a portion of a length l (FIG. 1B) of the vessel wall VW adjacent the distal portion 100. In some embodiments, the surface 101 shown in FIGS. 1A-1B can have other configurations. For example, in some embodiments the surface 101 can be perpendicular to a longitudinal axis of the delivery catheter and the exit port 121 can be positioned along the perpendicular surface.

The expansion lumen 130 can extend distally from the proximal portion of the delivery catheter to one or more transition elements (not shown) that are configured to fluidly couple the expansion lumen 130 to the expandable element 136. For example, in embodiments where the expandable element 136 is a balloon or similar inflatable structure, the expansion lumen 130 is fluidly coupled to the balloon via one or more inflation ports (not shown). Additionally, the expandable element 136 is positioned along the delivery catheter such that at least a portion of the expandable element 136 is circumferentially opposite a tissue engaging portion of the trough 112, as described in greater detail below. In the illustrated embodiment, the trough 112 has a main channel 113 surrounded by a bottom portion 115 and sidewalls 109 that extend upwardly from the bottom portion 115 with tissue engaging portions 114 along the sidewalls 109.

Referring to FIG. 1C, the transducer array 111 can include one or more transmitting groups 116 and one or more receiving groups 118. Each of the transmitting groups 116 can comprise one or more transducers 117 configured to transmit a signal (e.g., intravascular ultrasound ("IVUS") transducers, optical coherence tomography ("OCT") transducers, etc.), and each of the receiving groups 118 can comprise one or more transducers 119 configured to receive a reflected signal (e.g., IVUS transducers, OCT transducers, etc.). As shown in FIG. 1C, in some embodiments the trough 112 can include an ultrasonic backing material 122 adhered to the bottom portion 115, and the transducers 117, 119 can be coupled or fixed to the ultrasonic backing material 122. The individual transmitting groups 116 and/or the receiving groups 118 can include from one transducer to over 100 transducers (e.g., 128 transducers). Moreover, different transmitting groups can have different numbers of transducers, different receiving groups can have different numbers of receivers, and the transmitting groups 116 and the receiving groups 118 can have the same number and/or different numbers of transducers. In some embodiments, the trough 112 can include one or more transducers (or group(s) of transducers) configured to both transmit and receive signals.

The trough 112 and/or support 108 can include one or more channels 124 extending therethrough that are configured to receive one or more wires 126 extending distally from a proximal portion (not shown) of the delivery catheter to the transducers 117, 119. In some embodiments, the wires 126 can be coupled to a handle assembly (not shown) and/or a display (not shown) coupled to a proximal portion of the delivery catheter (e.g., directly via a cable and/or wirelessly via Bluetooth, radiofrequency ("RF") signals, Wi-Fi, etc.). The handle assembly and/or the display can include a controller having memory and processing circuitry. The controller can be configured to activate the transducers to emit signals and process the received signals to generate an image on the display and/or provide diagnostic or therapeutic information to the user, as described in greater detail below with reference to FIGS. 4A-5C.

Figure 1D:
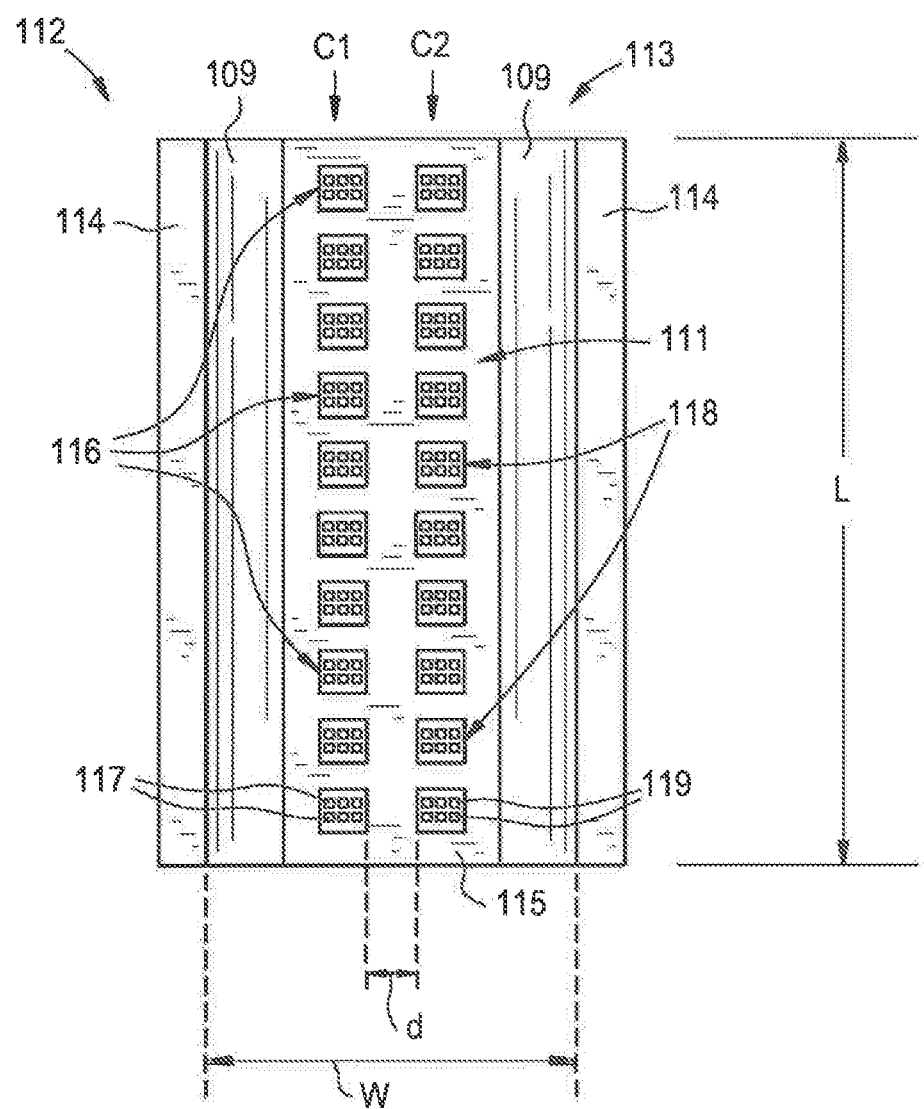
FIG. 1D is an isolated top view of the trough of FIGS. 1A-1C in accordance with an embodiment of the present technology.

FIG. 1D is an isolated top view of the trough 112. As shown in FIG. 1D, the transmitting groups 116 and the receiving groups 118 can be arranged in adjacent transmitting and receiving columns C1, C2, respectively, that extend along the length L of the trough 112. In some embodiments, the transmitting column C1 can be spaced apart from the receiving column C2 by a distance d of about 1 mm to about 10 mm. It will be appreciated that any arrangement and/or spacing of the transducers can be selected depending on the desired field of view. For example, the transmitting groups 116, the receiving groups 118, and/or the transducers 117, 119 can be sized and/or positioned along the trough 112 such that the individual fields of view of the transducers 117, 119 overlap and/or are close enough together such that the resulting images collectively represent an area of the vessel wall defined by the length L of the trough 112 aligned with the channel 113, as well as the width W of the trough 112. Although two columns and ten rows are shown in FIGS. 1A-1D, in other embodiments the trough 112 can have more or fewer columns (e.g., one column, three columns, four columns, etc.) and/or more or fewer rows (one row, five rows, 50 rows, 100 rows, etc.).

The trough 112 can be constructed from different materials depending on the imaging modality used. In embodiments utilizing intravascular ultrasound ("IVUS") transducers, the trough 112 material can have a high porosity to absorb sound waves and prevent reflections that can distort the image of the vessel wall VW (FIG. 1B). For example, the trough 112 may be made from a porous or semi-porous material such as a ceramic or a porous polymer or plastic. In some embodiments, the trough 112 can be made of one or more traditionally nonporous materials and be processed to have a predetermined porosity. For example, the trough 112 could be made from a three-dimensional printed polyether ether ketone ("PEEK") material or other plastic material that is built from layers deposited in a manner that leaves the material sufficiently porous. The trough 112 may also absorb waves if the material includes one or more imperfections that are smaller than the scale of the material, such as air bubbles, a reflective surface configured to cause local scattering, and the like. For example, in some embodiments the trough can include silicone cured such that one or more air bubbles are suspended within the silicone.

Figure 2A:
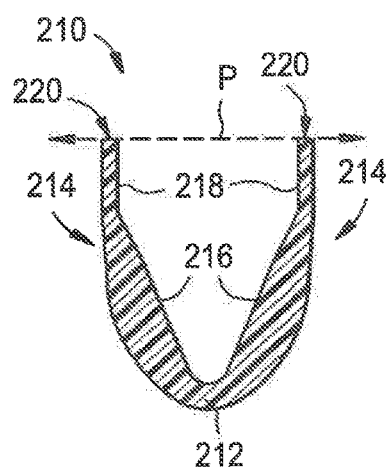
FIGS. 2A-2C are cross-sectional end views of troughs in accordance with embodiments of the present technology.
Figure 2B:
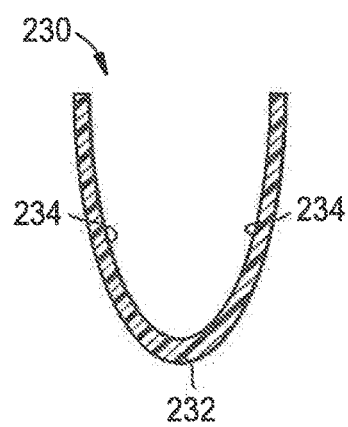
Figure 2C:
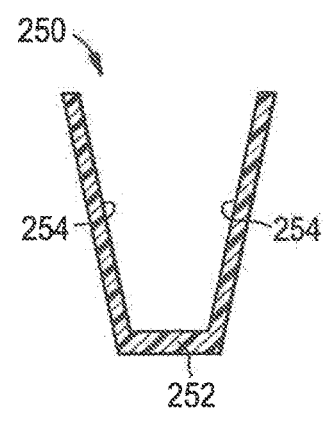

In addition to the material of the trough 112, the shape of the trough 112 can be selected to provide different acoustic properties. For example, FIGS. 2A-2C are cross-sectional end views of trough embodiments configured in accordance with the present technology. The transducers are not shown in FIGS. 2A-2C for ease of illustration. FIG. 2A shows one embodiment of a trough 210 having a curved inner surface at the bottom portion 212 and sidewalls 214. The inner surfaces of sidewalls 214 have a first linear section 216 extending upwardly from the bottom portion 212 and a second linear section 218 extending upwardly from the first linear section 216 and positioned at an angle relative to the first linear section 216. In other embodiments, the first and second sections 216, 218 can be linear, curved and/or have other suitable configurations. As shown in FIG. 2A, the second sections 218 can be generally perpendicular to a plane P running parallel to the vessel wall (not shown) when engaged by the tissue engaging portions 220. Such a configuration can provide a more direct angle for the emitted signals (e.g., sound waves) near the tissue engaging portions 220 of the trough 210, thereby providing a more distinct visual cue or landmark for the user at the junction between the tissue engaging portions 220 and the second sections 218.

In some embodiments, the inner surfaces of the sidewalls can have a generally continuous curved or linear configuration. For example, FIG. 2B shows a trough 230 having a semi-elliptical shape. In other embodiments, the trough 230 can have sidewalk with curved inner surfaces. In the embodiment of a trough 250 shown in FIG. 2C, the trough 250 has a polygonal shape (e.g., a half-hexagon shape, a half-square shape), etc. In other embodiments, the trough can have any suitable shape, size and/or configuration to improve the field of view and quality of the resulting image.

Figure 3A:
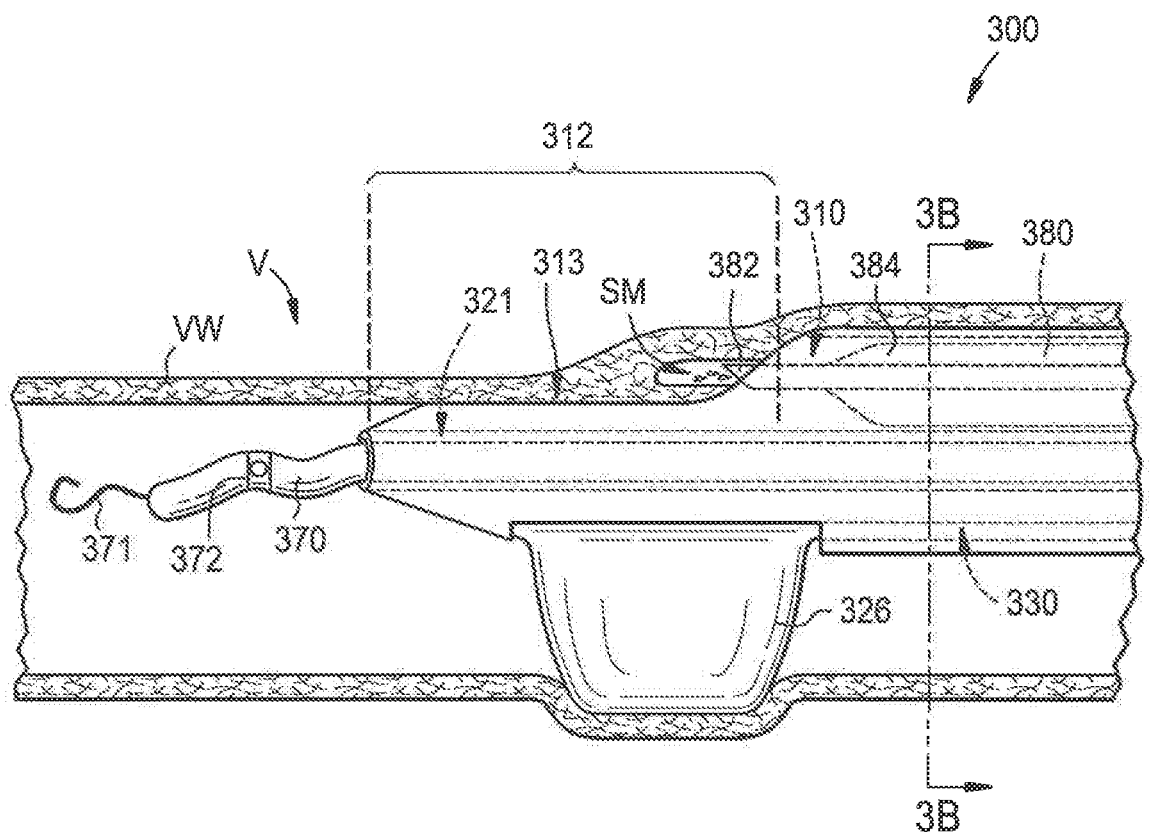
FIG. 3A is a side view of a delivery catheter in accordance with another embodiment of the present technology shown along with to a dissection assembly and a visualization device.
Figure 3B:
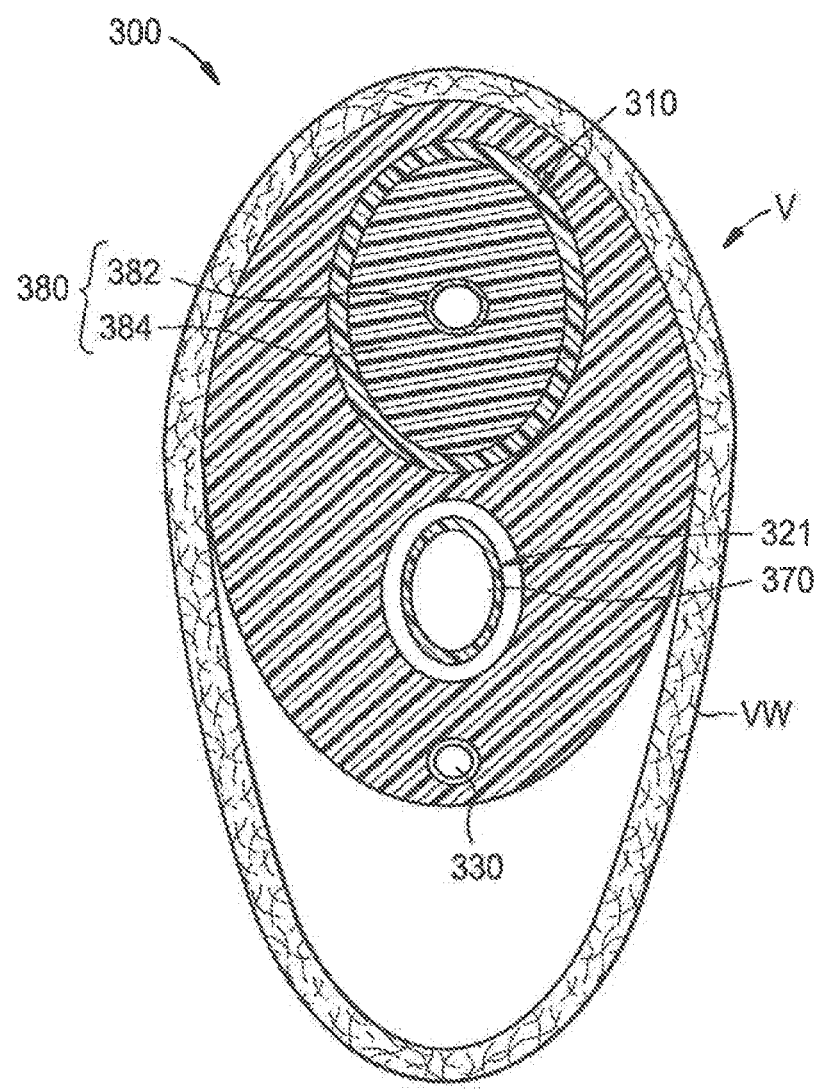
FIG. 3B is a cross-sectional end view of the treatment device of FIG. 3A taken along line 3B-3B.

FIG. 3A is a side view of a distal portion 300 of another embodiment of a delivery catheter in accordance with the present technology shown in an expanded state and positioned within a blood vessel V along with a dissection assembly 380 and a visualization catheter 370. FIG. 3B is a cross-sectional end view of the distal portion 300 of FIG. 3A taken along line 3B-3B. Referring to FIGS. 3A-3B together, the delivery catheter of FIGS. 3A-3B can be generally similar to the delivery catheter of FIGS. 1A-1D, except the delivery catheter of FIGS. 3A-3B includes a visualization lumen 321 configured to slidably receive a visualization catheter 370. The distal portion 300 can include an open trough 312 having a channel 313 configured to slidably receive the visualization catheter 370 therethrough. In the embodiment shown in FIGS. 3A-3B, the trough 312 does not include a transducer array. In other embodiments, however, the trough 312 may include one or more transducers.

The visualization catheter 370 can be an IVUS device, an OCT device, a direct visualization device and/or any other suitable visualization device. The visualization lumen 321 can extend distally from the proximal portion (not shown) of the delivery catheter to an exit port at the distal portion 300 that opens into the channel 313 of the trough 312. Although the embodiment of the delivery catheter shown in FIGS. 3A-3B does not include a guidewire lumen (and rather a guidewire 371 is fed through the visualization catheter 370), in other embodiments the treatment device 300 can also include a guidewire lumen.

As shown in FIG. 3A, the visualization catheter 370 can be advanced through the trough 312 such that an imaging portion 372 of the visualization catheter 370 is positioned distal to a distal terminus of the trough 312. In this "distal configuration," the visualization catheter 370 and/or the imaging portion 372 can be configured to rotate with respect to the vessel wall VW such that the visualization catheter 370 can image and/or analyze 360 degrees of the vessel wall VW. For example, such a method can be advantageous for diagnostic purposes and/or for selecting a dissection location. Other suitable exemplary devices, and systems, and methods for utilizing a visualization catheter for diagnostic and/or dissection location purposes is described in U.S. patent application Ser. No. 14/498,969, filed Sep. 26, 2014, which is incorporated by reference herein in its entirety.

Once a treatment location is identified, the distal portion 300 can be advanced to the treatment location, over the visualization catheter 370. Once at a location, the expandable element 326 can be expanded, causing the vessel wall VW to conform around the opposite side of the catheter, as shown in FIG. 3A. At this point, the dissection assembly 380 can be advanced distally through an exit port and into the vessel wall VW. The dissection assembly 380 can include a tubular, beveled needle 382 surrounded by a tubular support 384 having a tapered distal portion. Exemplary dissection assemblies can be found in any of the patent references incorporated herein, including U.S. Pat. No. 9,320,504, and incorporated herein by reference in its entirety. FIG. 3A shows an intermediate stage of a dissection procedure in which the needle 382 is being advanced within the vessel wall VW while ejecting fluid to create a sub-mural pocket SM within the vessel wall VW at a location that is longitudinally aligned with the trough 312. As such, during the wall dissection, the visualization catheter 370 can be positioned within the trough 312 such that the imaging portion 372 of the visualization catheter 370 is longitudinally aligned with at least a distal terminus of the needle 382. This way, a user can visualize the wall dissection.

In some embodiments, the transducer array 111 of FIGS. 1A-2C can be combined with the delivery catheter (and thus visualization catheter 370) of FIGS. 3A-3B. Such a configuration can be beneficial for capturing both close- and long-range images. For example, the transducer array 111 can be configured to resolve images within a relatively close distance (e.g., within about 1 mm to about 4 mm of the transducer array 111), and the visualization catheter 370 can be configured to resolve images at a relatively greater distance (e.g., about 4 mm to about 15 mm of the imaging device on the visualization catheter). The transducer array 111 can include the same and/or different visualization transducers as the visualization catheter 370. For example, in a particular embodiment, the visualization catheter 370 can be an IVUS device and the transducer array 111 can include OCT transducers (or vice versa). In yet other embodiments, the visualization catheter 370 can be an OCT device, and the transducer array 111 can include OCT transducers. In such embodiments, the optical transducers of the visualization catheter 370 can be configured to transmit/receive a first wavelength, and the optical transducers of the transducer array 111 can be configured to receive a second wavelength different than the first wavelength. Likewise, in those embodiments having an visualization catheter 370 and a transducer array 111 that includes ultrasound transducers, the ultrasound transducers of the visualization catheter 370 can be configured to transmit/receive a first wavelength, and the ultrasound transducers of the transducer array 111 can be configured to receive a second wavelength different than the first wavelength.

In those embodiments utilizing short-range ultrasound imaging (either with a visualization catheter or a transducer array), higher frequency transducers may be used to gain resolution over short distances. In some embodiments, the frequency can be between about 20 Hz and about 200 Hz. In other embodiments, the frequency can be between about 30 Hz and about 100 Hz. In yet other embodiments, the frequency can be between about 40 Hz and about 80 Hz. In a particular embodiment, the frequency can be between about 45 Hz and about 60 Hz.

In some embodiments, it may be beneficial to provide the user with an image of the vessel wall VW and/or the delivery catheter (and/or associated devices and systems) at the treatment site. The devices, systems, and methods of the present technology are configured to generate both two-dimensional (2D) and three-dimensional (3D) images. The imaging techniques of the present technology provide for real-time diagnostic and procedural monitoring capabilities.

Figure 4A:
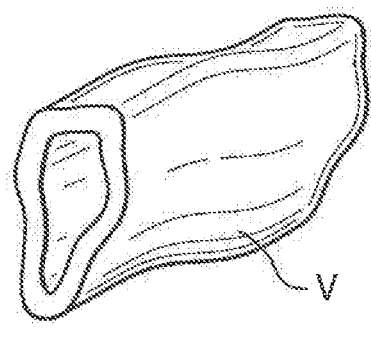
FIG. 4A is a schematic representation of a three-dimensional image of a portion of a blood vessel.
Figure 4B:
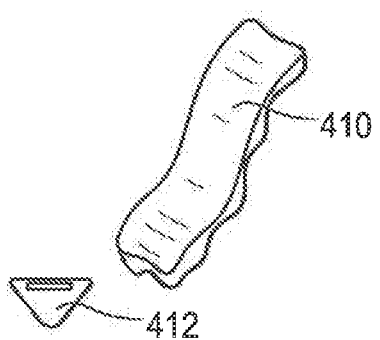
FIG. 4B is a schematic representation of generated images in accordance with the present technology.

In some embodiments, a 3D image of a portion of treatment site can be constructed with the 2D images gathered from the transducer array 111 (FIGS. 1A-1D) and/or the visualization catheter 370 (FIGS. 3A-3B). For example, the controller can receive the imaging data and splice the 2D images together (and/or multiple 3D images), with standard averaging techniques used to fill in areas of data overlap or locations where data is missing or shadowed. For example, FIG. 4A depicts a 360-degree, 3D reconstruction of segment of a vessel V. In one embodiment, such a 3D image is obtained by imaging the treatment site with the visualization catheter 370 (FIGS. 3A-3B) while drawing the visualization catheter 370 proximally from the distal configuration (or distally advancing the visualization catheter 370 from the visualization lumen 371) at a constant or predetermined speed. In some embodiments, one or more transducers of the transducer array can be configured to move relative to the delivery catheter (e.g., rotate, pivot, translate, etc.) and thus can also obtain such a "sweeping" shot. In some embodiments, an array or transducers (for example, as shown in FIG. 1D), can be automatically activated to send and receive signals at different specified times, at the same time (once and/or on a repeated schedule) to generate a static, dynamic, or real-time dynamic 3D image(s). Although the 3D image in FIG. 4A shows the exterior of the vessel, in other embodiments the 3D image can include all or a portion of the interior of the vessel or vessel wall. For example, as depicted schematically in FIG. 4B, the controller can combine 2D plane images 412 to create a 3D image 410 of the portion of the vessel wall targeted for, undergoing, or already completed dissection. It will be appreciated that the width of the portion corresponds to the width of the trough channel 113 (FIGS. 1A-1D) (e.g., the distance between the sidewalls 109 at the tissue engaging portions 114).

Figure 4C:
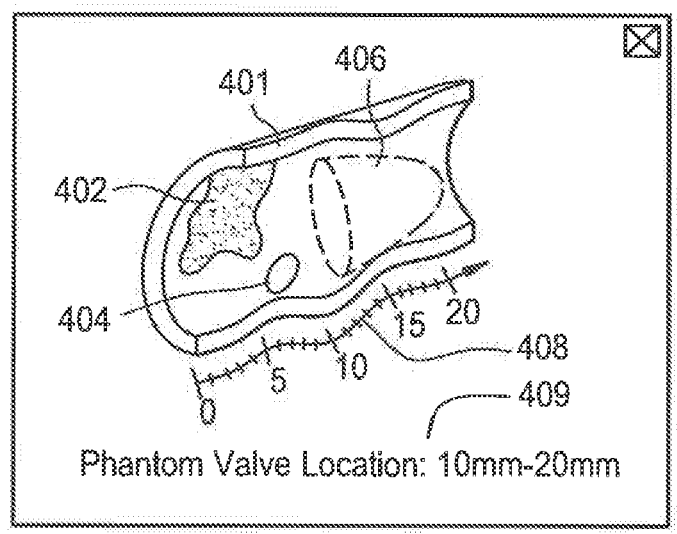
FIG. 4C is a schematic representation of an exemplary display screen in accordance with the present technology.

In some embodiments, the handle and/or display can be configured such that a user can toggle between desired 2D and 3D views, display one or more views simultaneously, scan across one or more views, zoom in/out on a particular feature, and/or rotate the 3D images. In a particular embodiment, the controller can include one or more algorithms that can analyze the 2D or 3D image, for example, by using patterns stored in the controller memory and associating certain patterns with certain known anatomical and/or device structures. The controller can then identify features of potential interest and provide an overlay on the image (e.g., as shown on the display) that provides additional information and/or clarification of the image. For example, as shown in FIG. 4C, the overlay may highlight certain scarring or fibrosis 402 present in the tissue, the presence of collateral vessels 404, and/or other anatomic features important to the particular diagnostic or procedure. In some embodiments, the overlay can identify different layers within the vessel wall, such as intima, media and adventitia. The overlay can call attention to various features using color coding, identifying symbols (e.g., arrows, circled portions, elevation lines, etc.), text, and/or numbers. Moreover, the overlay can include a length scale 408. For example, the length scale can be positioned along the axis of the displayed vessel. Similar overlays may also depict distances between features and/or the estimated size of particular features of interest.

In some embodiments, the overlay can include a "phantom valve" 406 (FIG. 4C) outline. In some embodiments, the user can choose the location of a phantom valve via a user interface (not shown), and that location may be displayed to the user with a text depiction 409. This location can then be stored in the memory such that, when the delivery catheter is delivered to the general vicinity of the treatment site, the controller can alert the user (e.g., via the display) as to where the delivery catheter should be positioned so as to be aligned with the phantom valve. For example, the controller can include an algorithm that analyzes the images and stores the locations of certain anatomical landmarks near the phantom valve site in the memory, as well as each landmark's location relative to the phantom valve site. In a particular embodiment, the controller can monitor the position of the delivery catheter (and/or components thereof) and compare that position to the position of the visualization catheter when imaging a desired treatment location. In other embodiments, the controller can indicate where to position the delivery catheter based on manual input from the user using standard sheath and catheter marking systems).

Figure 5:
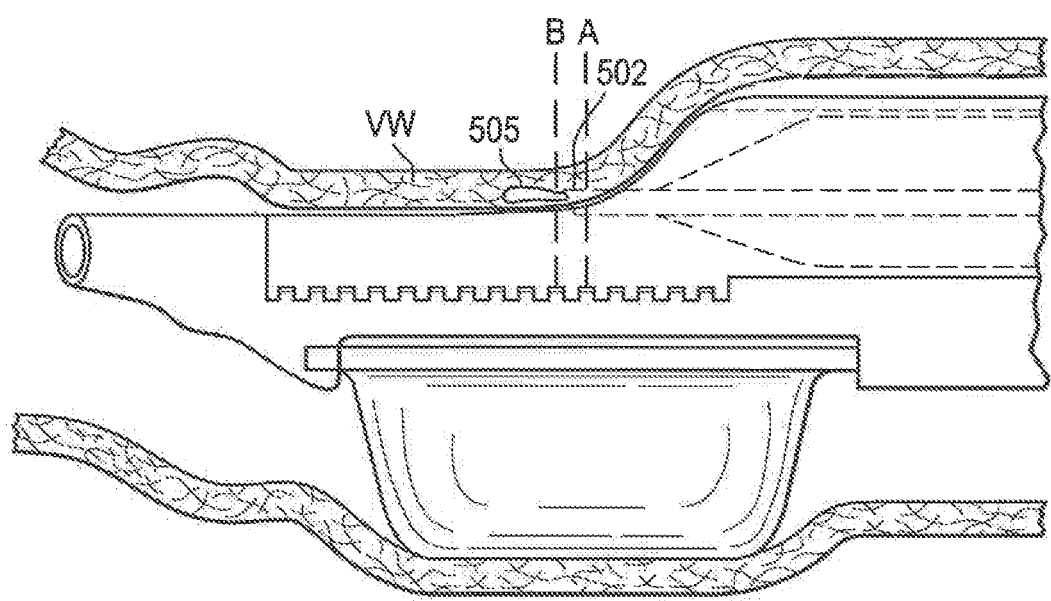
FIG. 5 is a partial cross-sectional side view of a distal portion of a delivery catheter in accordance with an embodiment of the present technology shown positioned within a blood vessel.

In any of the embodiments disclosed herein, it may be advantageous for automatic tracking of one or more imaging planes at the treatment site. FIG. 5 shows an embodiment in which the controller can activate (e.g., automatically or manually) one or more transducer(s) of the transducer array 111 at the same or different times to obtain images of different planes. For example, as shown in FIG. 5, the transducer array can image plane A at a first time, which can include the needle 502. Additionally or alternatively, the controller can activate the transducer(s) to image plane B at a second time, which can be distal to the needle 502 (e.g., to monitor a developing hydrodissection pocket 505 within the vessel wall VW). The first time and the second time can be the same time or different times. In some embodiments, the controller can display both plane A and plane B simultaneously. For example, the display can show plane A and plane B side-by-side. In a particular embodiment, the controller can automatically toggle between plane A and plane B. It will be appreciated that any number of planes can be imaged and/or displayed. In some embodiments, the controller can determine which plane to display based on the position of the needle 382 (FIGS. 3A-3B), for example, by utilizing algorithms and/or any number of distance-tracking devices built into the back end of the delivery catheter. In one embodiment, the controller can select which plane(s) to display based on pattern recognition. For example, it is known that a metal needle reflects more sound or light waves than does tissue, and the controller can include an algorithm that detects an image having bright spots (created by the reflection of the metal needle), label that image as the reference frame, and choose an imaging plane (and/or move the visualization catheter, transducer, and/or delivery catheter) relative to the reference frame location.

Although FIG. 5 shows the transducer array 111 performing selective activation of transducers to image various planes of view, the visualization catheter 370 can additionally or alternatively be used. For example, the visualization catheter 370 can be coupled to an actuator (not shown) (e.g., at the proximal portion of the delivery catheter) which can be configured to advance or retract the visualization catheter 370 to desired locations at the treatment site. In some embodiments, the desired locations can be determined manually or automatically during the procedure, and in some embodiments the desired locations can be on a pre-determined schedule.

Figure 6A:
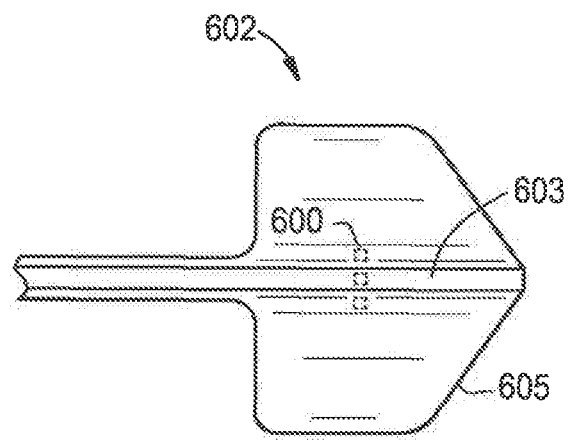
FIG. 6A is a top view of an expanded, semi-straightened pocket creation element in accordance with an embodiment of the present technology.
Figure 6B:
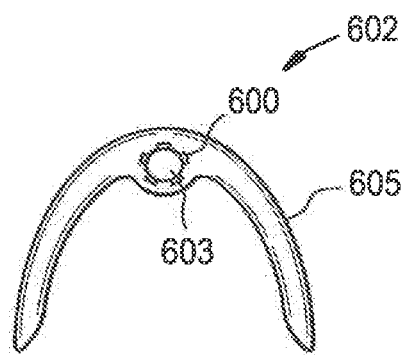
FIG. 6B is an end view of a pocket creation balloon in an expanded, unobstructed state, in accordance with an embodiment of the present technology.

In some embodiments, it may be beneficial to position an imaging device (e.g., a transducer) on the needle 382 and/or the dissection assembly 380 (FIGS. 3A-3B) such that the imaging is fully contained on the needle 382 (transmitting and receiving). In other embodiments, the transmission can occur at the needle 382, and the reception can occur at the dissection assembly 380. The imaging device can have other positions. For example, FIG. 6A is a top view of a pocket creation element 602 (e.g., a balloon, a wire cage, etc.) having an elongated shaft 603, an expandable element 605 coupled to the elongated shaft 603, and a plurality of imaging devices 600 positioned around the circumference of the elongated shaft 603. In FIG. 6A, the expandable element 605 is shown in an expanded, partially straightened configuration for ease of illustration. At least when the expandable element 605 is expanded, the imaging devices 600 can be positioned within the expandable element 605. As shown in the non-straightened end view of the pocket creation element 602 in FIG. 6B, the pocket creation element 602 can imitate the curvature of the vessel wall (not shown). In those embodiments where the expandable element 605 is a balloon, the material of the balloon can be selected to reduce scattering or reflections of the imaging wave. For example, the balloon can be inflated with saline, and all air bubbles can be removed from the inflation line.

III. CONCLUSION

Although the invention has been described in terms of particular embodiments and applications, one of ordinary skill in the art, in light of this teaching, can generate additional embodiments and modifications without departing from the spirit of or exceeding the scope of the exampled invention. Accordingly, it is to be understood that the drawings and descriptions herein are proffered by way of example to facilitate comprehension of the invention and should not be construed to limit the scope thereof.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. A system, comprising:
a delivery catheter configured to be intravascularly delivered to a dissection site within a blood vessel, the delivery catheter comprising a device lumen, a visualization lumen, and an open trough having a channel;
a dissection assembly having a distal terminus, wherein the dissection assembly is configured to extend through the device lumen of the delivery catheter; and
wherein—
the visualization lumen is configured to receive a visualization catheter having a distal end portion with an imaging portion,
the channel of the open trough is configured to allow the imaging portion to generate images of portions of a length of the vessel when the imaging portion is aligned with the channel during wall dissection.

2. The system of claim 1 wherein the distal terminus of the dissection assembly comprises a beveled needle, wherein the beveled needle and the imaging portion are configured to be in longitudinal alignment during wall dissection.

3. The system of claim 1, further comprising an actuator coupled to the visualization catheter and configured to be activated to automatically move the visualization catheter through the channel to predetermined locations during wall dissection.

4. The system of claim 1 wherein:
the dissection assembly comprises a needle configured to eject fluid to create a sub-mural pocket within the vessel wall and further configured to be advanced within a vessel wall while ejecting fluid; and
the imaging portion of the visualization catheter configured to be longitudinally aligned with the needle during wall dissection.

5. The system of claim 1 wherein the visualization lumen and the trough are configured to allow the visualization catheter to move longitudinally beyond a distal terminus of the trough to a position outside of the visualization lumen.

6. A system for visualization of intravascular creation of autologous valves, the system comprising:
a delivery catheter having a distal portion configured to be intravascularly advanced to a dissection site within a vessel, wherein the distal portion comprises—
an open trough including a channel;
a visualization lumen extending through the channel and configured to receive a visualization catheter having imaging portion for generating images of portions of a length of the vessel while the visualization catheter moves through the channel; and
a device lumen having an exit port; and
a dissection assembly configured to be advanced through the device lumen, wherein—
a distal terminus of the dissection assembly is configured to extend beyond the exit port into a vessel wall of the vessel and further configured to create a sub-mural pocket within the vessel wall, and
the imaging portion of the visualization catheter and the distal terminus of the dissection assembly are configured to be moved into longitudinal alignment with each other as the dissection assembly is advanced into the vessel wall during creation of the sub-mural pocket.

7. The system of claim 6 wherein the channel of the trough comprises an enclosed visualization lumen configured to receive the imaging portion of the visualization catheter as the imaging portion is distally advanced through the enclosed visualization lumen.

8. The system of claim 7 wherein the trough is configured to allow the imaging portion of the visualization catheter to move beyond a distal terminus of the trough to a position outside of the enclosed visualization lumen.

9. The system of claim 6 wherein the visualization lumen is configured to receive a guidewire before receiving the visualization catheter.

10. A system, comprising:
- a delivery catheter configured to be intravascularly delivered to a dissection site within a blood vessel, the delivery catheter comprising a device lumen, a visualization lumen, and an open trough having a channel;
- a dissection assembly having a distal terminus, wherein the dissection assembly is configured to extend through the device lumen of the delivery catheter; and
- a visualization catheter having a distal end portion with an imaging portion, wherein—
  - the visualization catheter is configured to extend through the visualization lumen and through the channel of the open trough,
  - the imaging portion is configured to generate images of portions of a length of the vessel while the imaging portion is aligned with the channel of the open trough, and
  - the imaging portion is further configured to be positioned into longitudinal alignment with the dissection assembly during wall dissection.

* * * * *